United States Patent
Stamboni et al.

(10) Patent No.: US 10,490,307 B1
(45) Date of Patent: Nov. 26, 2019

(54) COGNITIVE-BASED TOOLS FOR CARE AND CHARGE OF INCONTINENT INDIVIDUALS OR ANIMALS

(71) Applicant: International Business Machines Corporation, Armonk, NY (US)

(72) Inventors: Diane M. Stamboni, Poughkeepsie, NY (US); Kathleen Chalas, Wappingers Falls, NY (US); Orion Hayes, Poughkeepsie, NY (US); Nicholas Buonarota, Wappingers Falls, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/057,905

(22) Filed: Aug. 8, 2018

(51) Int. Cl.
*G16H 40/63* (2018.01)
*G06Q 10/10* (2012.01)
*G06N 20/00* (2019.01)

(52) U.S. Cl.
CPC ............ *G16H 40/63* (2018.01); *G06N 20/00* (2019.01); *G06Q 10/1093* (2013.01)

(58) Field of Classification Search
CPC .... G16H 40/63; G06N 20/00; G06Q 10/1093; G08B 21/20; G08B 23/00; A61B 5/20; A61B 5/002; A61B 5/202; A61B 5/207; A61B 5/208
USPC ... 340/539.11, 539.12, 573.1, 573.5, 286.07; 600/300, 301
See application file for complete search history.

(56) References Cited

U.S. PATENT DOCUMENTS

| | | | |
|---|---|---|---|
| 4,813,422 A | 3/1989 | Fisher et al. |
| 5,984,854 A | 11/1999 | Ishikawa et al. |
| 6,135,945 A | 10/2000 | Sultan |
| 6,498,953 B2 | 12/2002 | Roe et al. |

(Continued)

FOREIGN PATENT DOCUMENTS

| | | |
|---|---|---|
| WO | 2015/181836 A2 | 12/2015 |
| WO | 2017/087452 A1 | 5/2017 |
| WO | 2017/099571 A1 | 6/2017 |

OTHER PUBLICATIONS

Mell et al.; "The NIST Definition of Cloud Computing—Recommendations of the National Institute of Standards and Technology"; US Department of Commerce—National Institute of Standards and Technology; Sep. 2011; 7 pages.

*Primary Examiner* — Hung T Nguyen
(74) *Attorney, Agent, or Firm* — Cantor Colburn LLP; Teddi Maranzano (57) ABSTRACT

Provided are systems, methods, and media for assisting incontinent subjects. An example method includes receiving sensor readings from a sensor to obtain pressure readings from a bladder or bowels of a subject. A machine learning algorithm is executed to determine when incontinence of the subject is expected to occur. The machine learning algorithm establishes threshold(s) at which to notify an autonomous system, the subject, or a caretaker, in which are established based on a correlation between the received sensor readings and a frequency of undeterred accidents of the subject. An electronic warning is transmitted to the autonomous system, the subject, or the caretaker of the subject, indicating that incontinence is expected to occur in response to detecting at least one sensor reading that exceeds a threshold. Feedback is obtained and the threshold is adjusted via the machine learning algorithm based on the received feedback.

20 Claims, 7 Drawing Sheets

(56) References Cited

U.S. PATENT DOCUMENTS

| | | |
|---|---|---|
| 6,658,297 B2 | 12/2003 | Loeb |
| 6,659,936 B1 | 12/2003 | Furness et al. |
| 6,735,474 B1 | 5/2004 | Loeb et al. |
| 6,941,171 B2 | 9/2005 | Mann et al. |
| 7,319,386 B2 | 1/2008 | Collins, Jr. et al. |
| 8,043,213 B2 * | 10/2011 | Hatlestad ............. A61B 5/0031 |
| | | 600/300 |
| 9,185,489 B2 * | 11/2015 | Gerber ................. A61B 5/0031 |
| 9,460,262 B2 * | 10/2016 | Kaufman ............ G06F 19/3418 |
| 9,782,583 B2 | 10/2017 | Sharma |
| 9,913,608 B2 | 3/2018 | Lewis et al. |
| 2007/0058492 A1 | 3/2007 | Carley |
| 2014/0005493 A1 | 1/2014 | Kim et al. |
| 2016/0120455 A1 * | 5/2016 | Pop ........................ A61B 5/208 |
| | | 600/301 |
| 2017/0189684 A1 | 7/2017 | Weber et al. |
| 2017/0203100 A1 | 7/2017 | Imran |

\* cited by examiner

COGNITIVE-BASED TOOLS FOR CARE AND CHARGE OF INCONTINENT INDIVIDUALS OR ANIMALS

BACKGROUND

The present invention generally relates to tools for assisting incontinent subjects, and more specifically, to cognitive-based tools and methods for care and charge of incontinent individuals or animals.

Young children, animals, and adults with disabilities may have trouble communicating biological needs to those around them. For example, an adult suffering from the late stages of Amyotrophic Lateral Sclerosis (ALS) may not have the ability and/or strength to communicate, verbally or otherwise, the need to relieve themselves. Often times such individuals require assistance with that task. Young children and animals may also be unable to communicate, or be incognizant of their own need to relieve themselves, which may lead to unsanitary conditions if a caretaker is not aware of the problem until after the child or animal has defecated or urinated.

The phrase "machine learning" broadly describes a function of an electronic system that learns from data. A machine learning system, engine, or module can include a trainable machine learning algorithm that can be trained, such as in an external cloud environment, to learn functional relationships between inputs and outputs that are currently unknown.

SUMMARY

Embodiments of the present invention provide a computer-implemented method for assisting incontinent subjects. A non-limiting example of the computer-implemented method includes receiving, by a system comprising one or more processors, sensor readings from a sensor configured to obtain pressure readings from at least one of a bladder or bowels of a subject over time. The method includes executing, by the system, a machine learning algorithm to determine when incontinence of the subject is expected to occur. The machine learning algorithm establishes one or more thresholds at which to notify an autonomous system, the subject, and/or a caretaker of the subject, in which the one or more thresholds are established based, at least in part, on a correlation between the received sensor readings and a frequency of undeterred accidents of the subject. The method includes transmitting, by the system, an electronic warning to the autonomous system, the subject, and/or the caretaker of the subject, indicating that incontinence is expected to occur in response to detecting that at least one sensor reading of the received sensor readings is exceeding at least one threshold of the one or more thresholds. In some embodiments of the present invention, the method further includes obtaining feedback from the subject and then adjusting at least one threshold based on executing the machine learning algorithm in view of the received feedback.

Embodiments of the present invention provide a system for assisting incontinent subjects. The system includes one or more processors that are configured to perform a method. A non-limiting example of the method includes receiving, by the system, sensor readings from a sensor configured to obtain pressure readings from at least one of a bladder or bowels of a subject over time. The method includes executing, by the system, a machine learning algorithm to determine when incontinence of the subject is expected to occur. The machine learning algorithm establishes one or more thresholds at which to notify an autonomous system, the subject, and/or a caretaker of the subject, in which the one or more thresholds are established based, at least in part, on a correlation between the received sensor readings and a frequency of undeterred accidents of the subject. The method includes transmitting, by the system, an electronic warning to the autonomous system, the subject, and/or the caretaker of the subject, indicating that incontinence is expected to occur in response to detecting that at least one sensor reading of the received sensor readings is exceeding at least one threshold of the one or more thresholds. In some embodiments of the present invention, the method further includes obtaining feedback from the subject and then adjusting at least one threshold based on executing the machine learning algorithm in view of the received feedback.

Embodiments of the invention provide a computer program product for assisting incontinent subjects, the computer program product comprising a computer readable storage medium having program instructions embodied therewith. The program instructions are executable by a system comprising one or more processors to cause the system to perform a method. A non-limiting example of the method includes receiving, by the system, sensor readings from a sensor configured to obtain pressure readings from at least one of a bladder or bowels of a subject over time. The method includes executing, by the system, a machine learning algorithm to determine when incontinence of the subject is expected to occur. The machine learning algorithm establishes one or more thresholds at which to notify an autonomous system, the subject, and/or a caretaker of the subject, in which the one or more thresholds are established based, at least in part, on a correlation between the received sensor readings and a frequency of undeterred accidents of the subject. The method includes transmitting, by the system, an electronic warning to the autonomous system, the subject, and/or the caretaker of the subject, indicating that incontinence is expected to occur in response to detecting that at least one sensor reading of the received sensor readings is exceeding at least one threshold of the one or more thresholds. In some embodiments of the present invention, the method further includes obtaining feedback from the subject and then adjusting at least one threshold based on executing the machine learning algorithm in view of the received feedback.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagram or the operations described therein without departing from the spirit of the invention. For instance, the actions can be performed in a differing order or actions can be added, deleted, or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems; storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
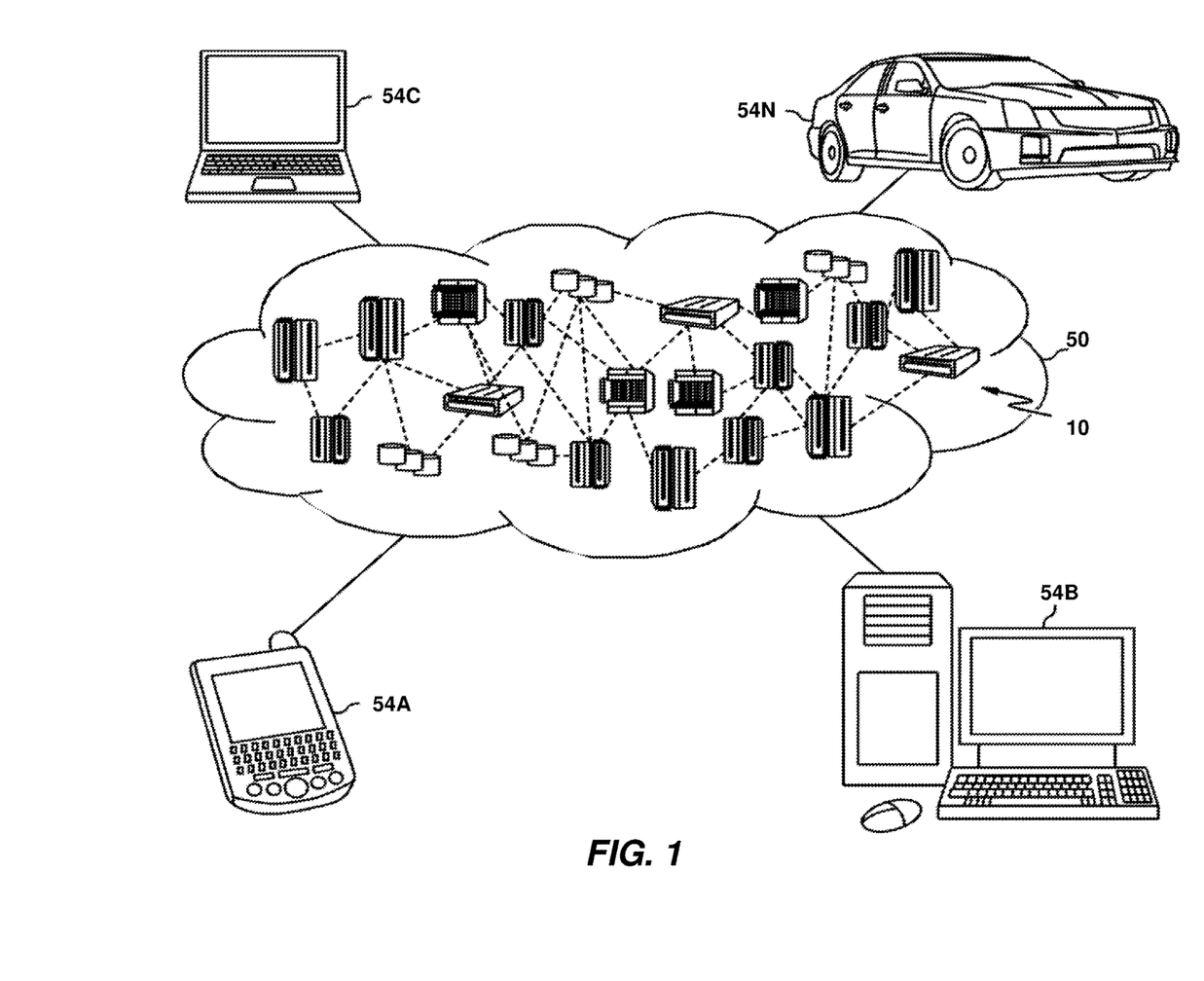
FIG. 1 depicts a cloud computing environment according to one or more embodiments of the present invention.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms, and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
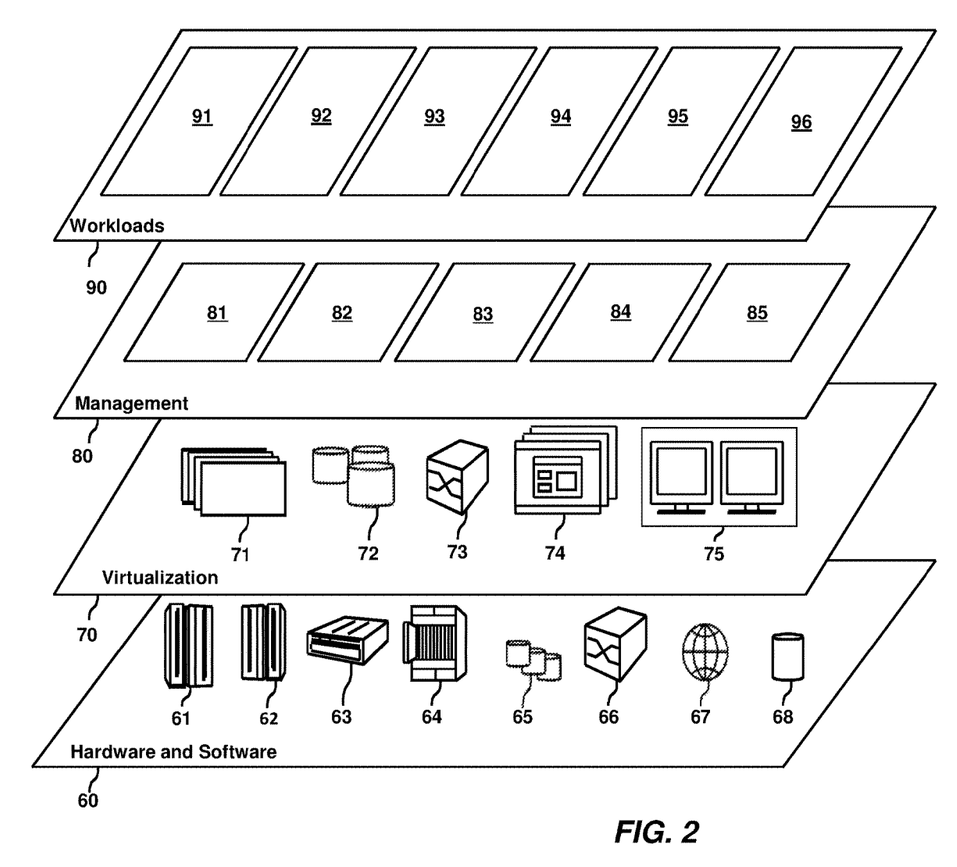
FIG. 2 depicts abstraction model layers according to one or more embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and incontinence data processing 96.

Turning now to an overview of technologies that are more specifically relevant to aspects of the invention, as noted above, young children, animals, and adults with disabilities may have trouble communicating biological needs to those around them. For example, an adult suffering from the late stages of Amyotrophic Lateral Sclerosis (ALS) may not have the ability and/or strength to communicate, verbally or otherwise, the need to relieve themselves. Often times such individuals require assistance with that task. Young children and animals may also be unable to communicate, or be incognizant of their own need to relieve themselves, which may lead to unsanitary conditions if a caretaker is not aware of the problem until after the child or animal has defecated or urinated.

Turning now to an overview of the aspects of the invention, one or more embodiments of the invention address the above-described shortcomings of the prior art by providing machine learning tool that is capable of assisting incontinence subjects (e.g., adults, children, animals). For example, in some embodiments of the present invention, a pressure sensor is operatively connected to a subject's bladder and/or bowels, in which the pressure sensor is configured to be in communication (e.g., wireless or wired communication) with an assistance system. In some embodiments of the present invention, the assistance system is configured to receive a sensor reading and compare the sensor reading against previously attained data in conjunction with demographic data to establish one or more thresholds at which to transmit a warning to a specified recipient as to when incontinence of the subject is expected to occur. In some embodiments of the present invention, the recipient is the subject him/herself or a caretaker. In some embodiments of the present invention, the recipient is an autonomous system (e.g., autonomous robot and/or medical device), a social media platform, and/or one or more human caretakers of the subject. In some embodiments of the present invention, the system is configured to obtain feedback after transmitting a warning and then to adjust the one or more thresholds in view of the feedback.

The above-described aspects of the invention address the shortcomings of the prior art by providing a system that is capable of helping a subjects relieve themselves before having an accident by notifying an autonomous system, the subject, a caretaker of the subject, a social media platform, and/or an autonomous system prior to when the incontinence is expected to occur. Feedback is then received to improve future predictions.

Figure 3:
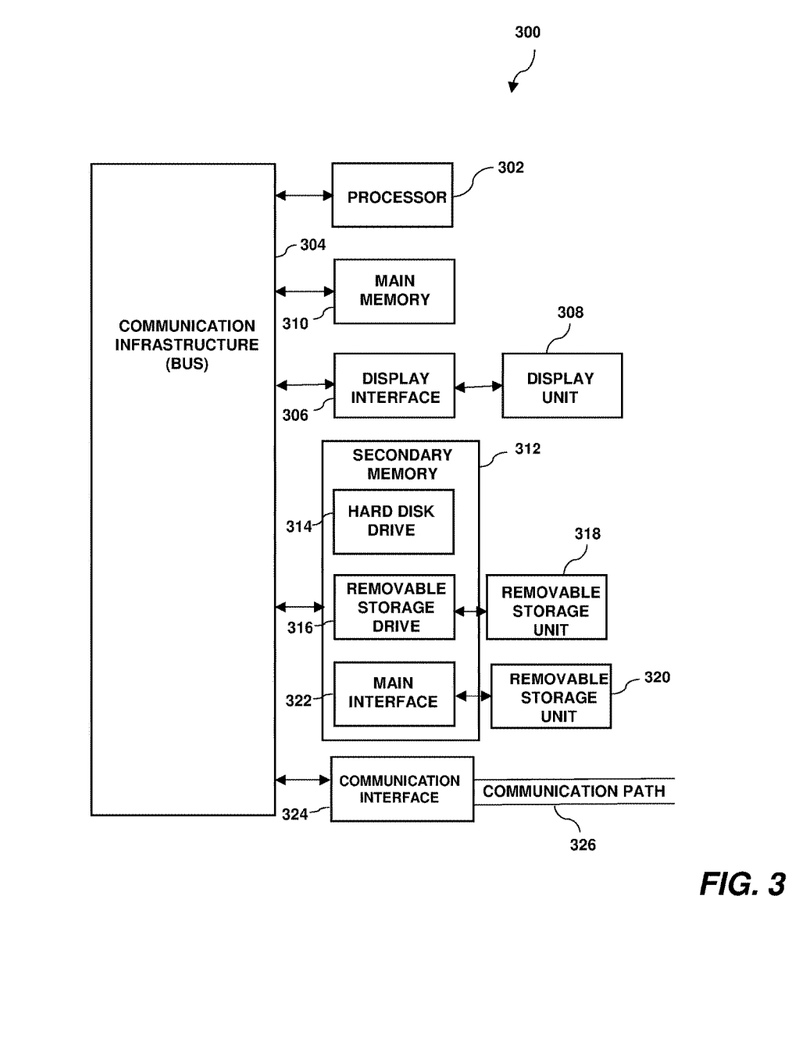
FIG. 3 depicts an exemplary computer system capable of implementing one or more embodiments of the present invention.

Turning now to a more detailed description of aspects of the present invention, FIG. 3 illustrates a high-level block diagram showing an example of a computer-based system 300 that is useful for implementing one or more embodiments of the invention. Although one exemplary computer system 300 is shown, computer system 300 includes a communication path 326, which connects computer system 300 to additional systems and may include one or more wide area networks (WANs) and/or local area networks (LANs) such as the internet, intranet(s), and/or wireless communication network(s). Computer system 300 and additional systems are in communication via communication path 326, (e.g., to communicate data between them).

Computer system 300 includes one or more processors, such as processor 302. Processor 302 is connected to a communication infrastructure 304 (e.g., a communications bus, cross-over bar, or network). Computer system 300 can include a display interface 306 that forwards graphics, text, and other data from communication infrastructure 304 (or from a frame buffer not shown) for display on a display unit 308. Computer system 300 also includes a main memory 310, preferably random access memory (RAM), and may also include a secondary memory 312. Secondary memory 312 may include, for example, a hard disk drive 314 and/or a removable storage drive 316, representing, for example, a floppy disk drive, a magnetic tape drive, or an optical disk drive. Removable storage drive 316 reads from and/or writes to a removable storage unit 318 in a manner well known to those having ordinary skill in the art. Removable storage unit 318 represents, for example, a floppy disk, a compact disc, a magnetic tape, or an optical disk, etc., which is read by and written to by a removable storage drive 316. As will be appreciated, removable storage unit 318 includes a computer readable medium having stored therein computer software and/or data.

In some alternative embodiments of the invention, secondary memory 312 may include other similar means for allowing computer programs or other instructions to be loaded into the computer system. Such means may include, for example, a removable storage unit 320 and an interface 322. Examples of such means may include a program package and package interface (such as that found in video game devices), a removable memory chip (such as an EPROM or PROM) and associated socket, and other removable storage units 320 and interfaces 322 which allow software and data to be transferred from the removable storage unit 320 to computer system 300.

Computer system 300 may also include a communications interface 324. Communications interface 324 allows software and data to be transferred between the computer system and external devices. Examples of communications interface 324 may include a modem, a network interface (such as an Ethernet card), a communications port, or a PCM-CIA slot and card, etc. Software and data transferred via communications interface 324 are in the form of signals which may be, for example, electronic, electromagnetic, optical, or other signals capable of being received by communications interface 324. These signals are provided to communications interface 324 via communication path (i.e., channel) 326. Communication path 326 carries signals and may be implemented using a wire or cable, fiber optics, a phone line, a cellular phone link, an RF link, and/or other communications channels.

In the present disclosure, the terms "computer program medium," "computer usable medium," and "computer readable medium" are used to generally refer to media such as main memory 310 and secondary memory 312, removable storage drive 316, and a hard disk installed in hard disk drive 314. Computer programs (also called computer control logic) are stored in main memory 310, and/or secondary memory 312. Computer programs may also be received via communications interface 324. Such computer programs, when run, enable the computer system to perform the features of the present disclosure as discussed herein. In particular, the computer programs, when run, enable processor 302 to perform the features of the computer system. Accordingly, such computer programs represent controllers of the computer system.

Figure 4:
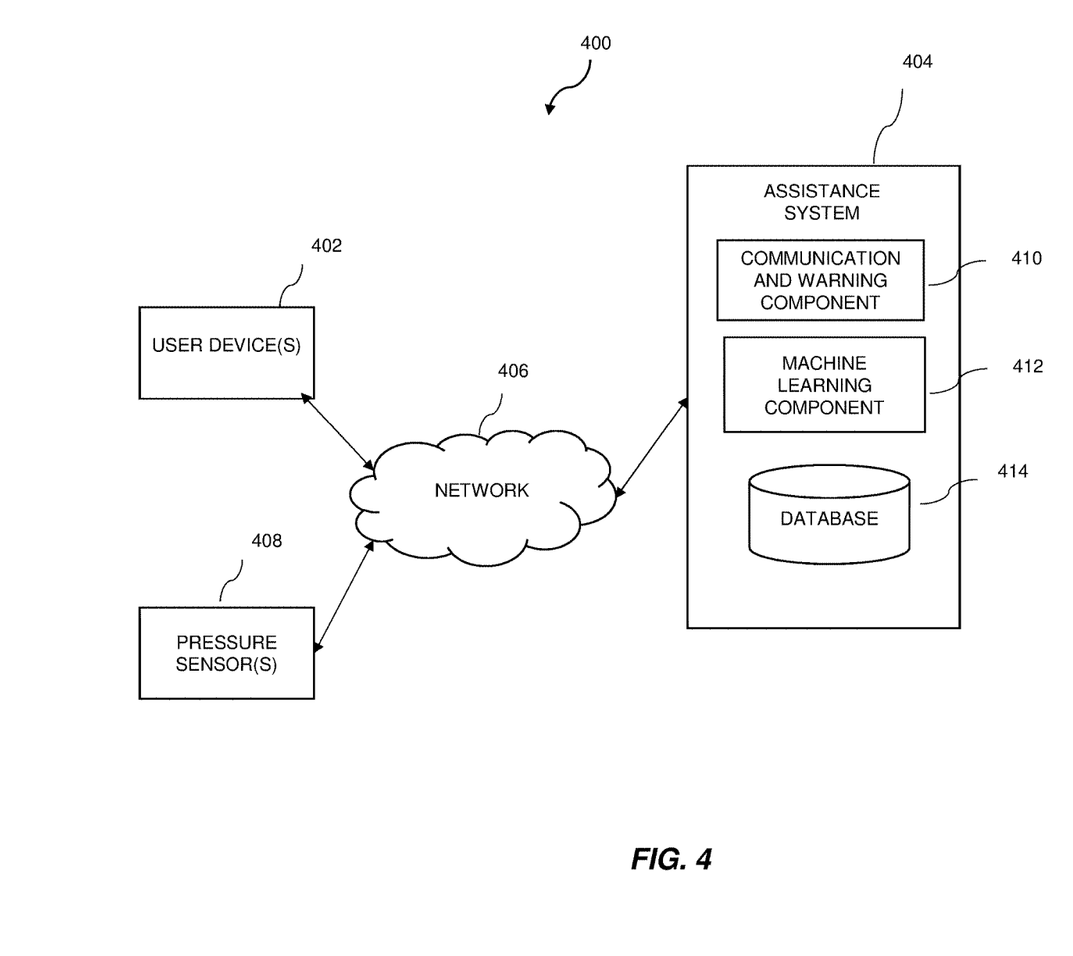
FIG. 4 depicts an example distributed environment in accordance with one or more embodiments of the present invention.

Referring now to FIG. 4, an example distributed environment 400 is presented for assisting incontinent subjects such as children, adults, animals. Distributed environment 400 includes one or more user devices 402, an assistance system 404, and one or more pressure sensor(s) 408, which are interconnected via network 406. FIG. 4 provides an illustration of only one example system and does not imply any limitation with regard to other systems in which different embodiments of the present invention may be implemented. Various suitable modifications to the depicted environment may be made, by those skilled in the art, without departing from the scope of the invention as recited by the claims. For example, in some embodiments of the present invention, the user devices 402 include the pressure sensors 408.

Assistance system 404 includes a communication and warning component 410, a machine learning component 412, and a database 414. In some embodiments of the present invention, communication and warning component 410, machine learning component 412, and/or database 414 are interconnected via a communication infrastructure 304 and/or communication path 326. Assistance system 404 may have internal and external hardware components, such as those depicted and described above with respect to FIG. 3.

Assistance system 404 is a machine learning system that can be utilized to solve a variety of technical issues (e.g., learning previously unknown functional relationships) in connection with technologies such as, but not limited to, machine learning technologies, video processing technologies, object generalization technologies, data analytics technologies, data classification technologies, data clustering technologies, recommendation system technologies, signal processing technologies, and/or other digital technologies. Assistance system 404 employs hardware and/or software to solve problems that are highly technical in nature, that are not abstract and that cannot be performed as a set of mental acts by a human.

Machine learning is often employed by numerous technologies to determine inferences and/or relationships among digital data such as sensor data. For example, machine learning technologies, signal processing technologies, image processing technologies, data analysis technologies, and/or other technologies employ machine learning models to analyze digital data, process digital data, determine inferences from digital data, and/or determine relationships among digital data. Machine learning functionality can be implemented using an artificial neural network (ANN) having the capability to be trained to perform a currently unknown function. In machine learning and cognitive science, ANNs are a family of statistical learning models inspired by the biological neural networks of animals, and in particular the brain. ANNs can be used to estimate or approximate systems and functions that depend on a large number of inputs.

ANNs can be embodied as so-called "neuromorphic" systems of interconnected processor elements that act as simulated "neurons" and exchange "messages" between each other in the form of electronic signals. Similar to the so-called "plasticity" of synaptic neurotransmitter connections that carry messages between biological neurons, the connections in ANNs that carry electronic messages between simulated neurons are provided with numeric weights that correspond to the strength or weakness of a given connection. The weights can be adjusted and tuned based on experience, making ANNs adaptive to inputs and capable of learning. For example, an ANN for handwriting recognition is defined by a set of input neurons that can be activated by the pixels of an input image. After being weighted and transformed by a function determined by the network's designer, the activation of these input neurons are then passed to other downstream neurons, which are often referred to as "hidden" neurons. This process is repeated until an output neuron is activated. The activated output neuron determines which character was read.

In certain embodiments of the invention, some or all of the processes performed by assistance system 404 are performed by one or more specialized computers for carrying out defined tasks related to machine learning. In some embodiments of the invention, assistance system 404 and/or components of the system are employed to solve new problems that arise through advancements in technologies mentioned above.

In general, assistance system 404 is a cognitive-based tool that, in some embodiments of the present invention, communicates with pressure sensor 408 that is operatively coupled to the subject's bladder and/or bowels. In some embodiments of the present invention, whenever there is an increase or decrease in pressure, pressure sensor 408 sends data on the amount of pressure in the bladder and/or bowels to the assistance system 404. Assistance system 404 then detects the subject's need to relieve themselves based on all the gathered information, and sends a notification to a specified recipient (e.g., user device 402). In some embodiments of the present invention, the notification takes the form of one or more of a social media post, social media message, text message, phone alert, tweet, email, etc. In some embodiments of the present invention, the notification further or alternatively takes the form of an alert that is transmitted to digital contexts via WiFi-direct to an electronic device other than a smartphone when the caretaker is busy interacting with the electronic device (e.g., caretaker is busy playing a game on a desktop computer, watching a television show on a television set, etc.). When the notification is received, a recipient such as the subject, the caretaker, or autonomous system (e.g., robot) can assist the subject in relieving themselves appropriately.

In some embodiments of the present invention, assistance system 404 utilizes machine learning to determine the appropriate threshold at which to notify a recipient and/or to determine which recipients to transmit an electronic warning to. For example, in some embodiments of the present invention, user feedback can be used to teach assistance system 404 (e.g., machine learning component 412) to wait for a stronger sensor signal before issuing a warning. On the other hand, if the subject has an accident as a resulting of having waited too long, the user feedback can be used to teach assistance system 404 (e.g., machine learning component 412) that a notification needs to be transmitted sooner and/or more often.

In some embodiments of the present invention, as machine learning component 412 learns the threshold of a given subject, machine learning component 412 also determines and/or selects between different levels of notification to send. For example, in some embodiments of the present invention, if a given subject is able to relieve themselves if prompted, a lower level notification may be utilized as there would be no need to drop everything and attend to them immediately. On the other hand, in some embodiments of the present invention, if the subject is visibly uncomfortable, showing other distress (e.g., in the case of restroom training) or nearing an accident, then stronger, more persistent notifications may be issued and thus a higher level notification may be utilized.

In some embodiments of the present invention, assistance system 404 is a standalone computing device, a management server, a web server, a mobile computing device, or other suitable electronic device and/or computing system capable of receiving, sending, and processing data. In some embodiments of the present invention, assistance system 404 is a server computing system utilizing multiple computers, such as in cloud computing environment 50. In some embodiments of the present invention, assistance system 404 is a laptop computer, a tablet computer, a netbook computer, a personal computer (PC), a desktop computer, a personal digital assistant (PDA), a smart phone, or other suitable programmable electronic device capable of communicating with user device 402, pressure sensors 408, and other computing devices (not shown) within distributed environment 400 via network 406. In some embodiments of the present invention, assistance system 404 is a computing system utilizing clustered computers and components (e.g., database server computers, application server computers, etc.) that act as a single pool of seamless resources that are accessible within distributed environment 400. Assistance system 404 may have internal and external hardware components, such as those depicted and described above with respect to FIG. 3.

Network 406 can be, for example, a telecommunications network, a local area network (LAN), a wide area network (WAN), such as the Internet, or a combination of the three, and can include wired, wireless, or fiber optic connections. Network 406 can include one or more wired and/or wireless networks that are capable of receiving and transmitting data, voice, and/or video signals, including multimedia signals that include voice, data, and video information. In general, network 406 can be any suitable combination of connections and protocols that can support communications between user device 402, pressure sensor 408, assistance system 404, and/or other computing devices (not shown) within a distributed environment 400. In some embodiments of the present invention, distributed environment 400 is implemented as part of a cloud computing environment such as cloud computing environment 50 (FIG. 1).

User device 402 is configured to allow users (e.g., human subjects and/or caretakers) to send and/or receive information from user device 402 to assistance system 404 and pressure sensors 408, which in turn allows users to access communication component 410, machine learning component 412, and database 414. In some embodiments of the present invention, database 414 is configured to store data that is obtained from user device 402, pressure sensors 408, and/or assistance system 404 (e.g., demographic data, prior sensor readings of the subject, feedback data of the subject, etc.)

In some embodiments of the present invention, user device 402 is configured to gather user input data, biometric data, audible data, and/or visual data. In some embodiments of the present invention, user device 402 is configured to capture audio, images, and/or video of the user (e.g., via a microphone and/or camera of user device 402). In some embodiments of the present invention, user device 402 includes a GPS device for tracking a location of the user device 402. In some embodiments of the present invention, user device 402 executes applications such as calendar applications, remote access applications and social media applications, and allows the user to provide feedback to assistance system 404.

In some embodiments of the present invention, user device 402 is a laptop computer, a tablet computer, a netbook computer, a personal computer (PC), a desktop computer, a personal digital assistant (PDA), a smart phone, an internet-of-things (IoT) enabled device, and/or other suitable programmable electronic devices capable of communicating with various components and devices within distributed environment 400. In some embodiments of the present invention, user device 402 is a programmable electronic mobile device or a combination of programmable electronic mobile devices capable of executing machine readable program instructions and communicating with other computing devices (not shown) within distributed environment 400. In some embodiments of the present invention, user device 402 may include internal and external hardware components, such as those depicted and described above with respect to FIG. 3.

Pressure sensors 408 are sensors that are operatively coupled to the subject such that at least one of a bladder or bowels of the subject may be monitored over time. Various suitable existing pressure sensors 408 can be implanted within a body of the subject and be used to communicate the sensor information from various medical devices to the subject (e.g., user device 402) and/or to assistance system 404 in a wireless or wired manner. In some embodiments of the present invention pressure sensors 408 are sensors that are not specifically implanted within the body of the subject, but rather are sensors that are positioned outside the body of the subject and obtain sensor readings from an outside body region such as from the abdomen of the subject. Various suitable pressure sensors 408 as known to those having ordinary skill in the art may be utilized in one or more embodiments of the present invention. As noted above, in some embodiments of the present invention, user device 402 and pressure sensors 408 are not separate devices, but rather user device 402 includes pressure sensors 408.

In the example depicted in FIG. 4, assistance system 404 is configured to receive sensor readings from one or more pressure sensors 408 (e.g., via communication and warning component 410), in which pressure sensors 408 are configured to obtain pressure readings from at least one of a bladder or bowels of a subject over time. After receiving the sensor readings, assistance system 404 executes a machine learning algorithm to determine when incontinence of the subject is expected to occur (e.g., via machine learning component 412). The machine learning algorithm establishes one or more thresholds at which to notify a recipient such as the subject, a caretaker of the subject, or an autonomous system (e.g., robotic system). In some embodiments of the present invention, the one or more thresholds are established based, at least in part, on a correlation between the received sensor readings and a frequency of undeterred accidents of the subject. Based on the established thresholds, assistance system 404 then detects when and/or whether one or more sensor readings of the received sensor readings are exceeding at least one threshold of the one or more thresholds. In response to detecting that at least one sensor reading of the received sensor readings is exceeding at least one threshold of the one or more thresholds, assistance system 404 then transmits an electronic warning to the recipient (e.g., from communication and warning component 410 to user device 402), in which the electronic warning indicates that incontinence is expected to occur. In some embodiments of the present invention, the electronic warning further includes an indication of the location of the subject (e.g., GPS coordinates, address information, nearest landmarks, etc.). In some embodiments of the present invention, the location information is obtained from the user device of the subject (e.g., user device(s) 402).

In some embodiments of the present invention, the transmitting of the electronic warning to the recipient, such as the autonomous system, the subject, and/or the caretaker of the subject, includes assistance system 404 obtaining location information regarding the location of the subject and the locations of a plurality of caretakers of the subject. In some embodiments of the present invention, the locations of the plurality of caretakers and the location of the subject are obtained from respective user device 402 of the subject and caretakers (e.g. GPS coordinates, address information, nearest landmarks, etc.). Assistance system 404 is configured to identify which of the plurality of caretakers the warning transmission should be sent to. For example, in some embodiments of the present invention, assistance system 404 is configured to determine which of the plurality of caretakers is presently located nearest to the subject, in which the identifying is based on the locations of the plurality of caretakers and the location of the subject. The electronic warning is then transmitted to the identified caretaker.

In some embodiments of the present invention, assistance system 404 is configured to identify which of the plurality of caretakers the transmission should be sent to by further obtaining calendar information for each of the plurality of caretakers, in which the calendar information includes a location of an event. Assistance system 404 is configured to identify a subset of the plurality of caretakers that are not presently located at the event, in which the identifying of the subset of caretakers is based on matching the locations of the plurality of caretakers to the location of the event. Assistance system 404 then identifies, based on the locations of the plurality of caretakers and the location of the subject, which caretaker of the subset of caretakers is presently located nearest to the subject. The electronic warning is then transmitted to the identified caretaker.

In some embodiments of the present invention, after assistance system 404 transmits the electronic warning, assistance system 404 obtains feedback from the autonomous system, the subject, and/or the caretaker regarding whether the warning was effective. Based on the effectiveness of the warning, assistance system 404 then determines via machine learning whether one or more thresholds are to be adjusted to provide more accurate future predictions of when incontinence of the subject is expected to occur. For example in some embodiments of the present invention, assistance system 404 is configured to adjust at least one threshold in response to the feedback indicating that the subject was incontinent at a time prior to when the electronic warning was transmitted such that the autonomous system, the subject, and/or the caretaker is notified at an earlier time.

Figure 5:
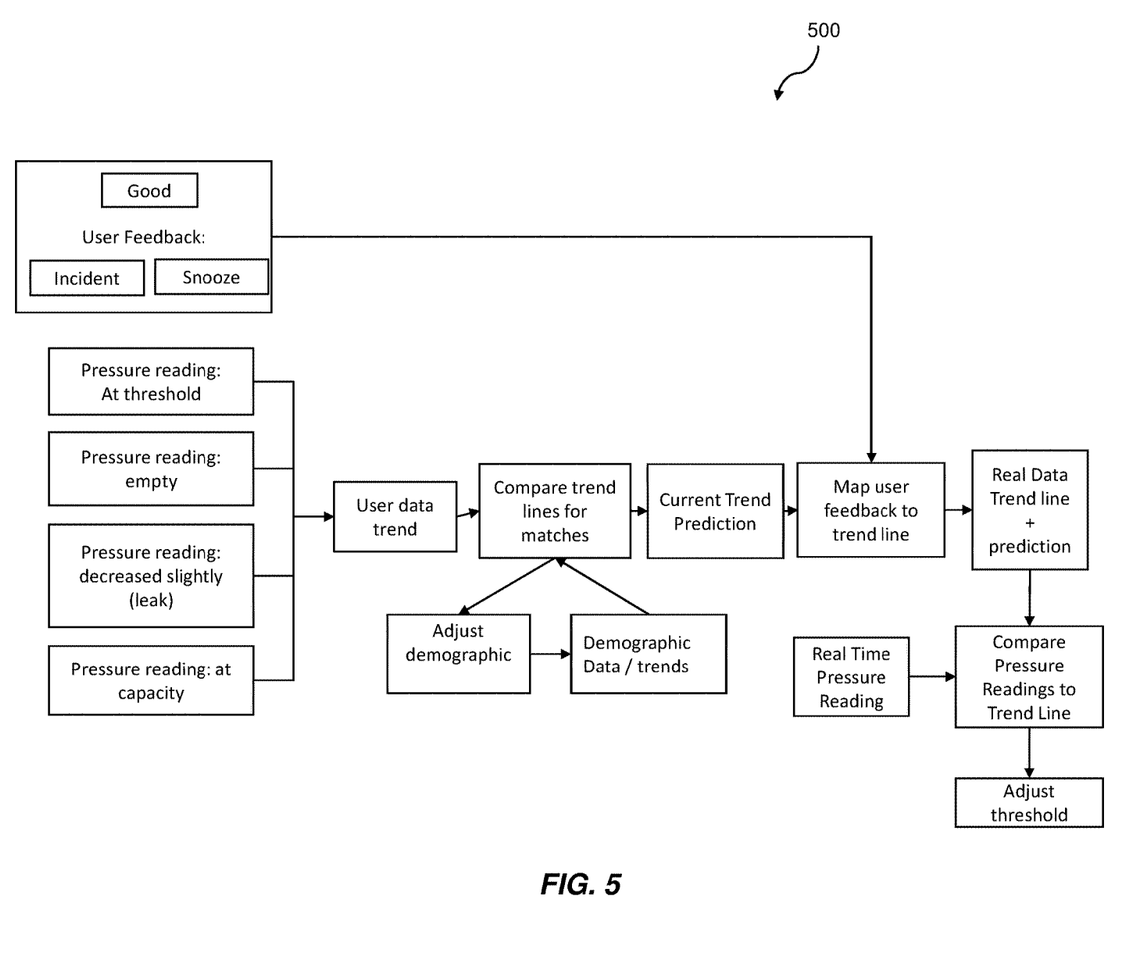
FIG. 5 depicts a diagram illustrating an example methodology of a machine learning component in accordance with one or more embodiments of the present invention.

FIG. 5 depicts a flow diagram 500 illustrating an example implementation of machine learning component 412 of assistance system 404 in accordance with one or more embodiments of the present invention. Pressure reading data is obtained for a first time period from pressure sensors operatively coupled to a user (e.g., the subject). This pressure data may be historical data that is obtained. In some embodiments of the present invention, the pressure reading data includes information such as, for example, whether a particular pressure reading is at or exceeds one or more established thresholds, whether the bladder or bowels are empty, whether a decrease in pressure is detected in bladder or bowels such as during a leak, and/or whether the pressure of the bladder or bowels is at capacity. A user data trend is generated from the received pressure reading data to record correlations with frequencies of undeterred accidents (e.g., stored in database 414). In some embodiments of the present invention, the frequency of undeterred accidents is established by assistance system 404 based on received user feedback that links pressures detecting at various points in time with the feedback indicating whether an accident occurred at those points in time. Anonymized demographic data and/or anonymized demographic data trends are obtained from a plurality of other users (e.g., other subjects and then the anonymized demographic data and/or anonymized demographic data trends are compared to the user data trend to identify matches. In some embodiments of the present invention, the demographic data and/or anonymized demographic data trends are updated to include data from the generated user data trend.

The identified matches between the user data trend and the anonymized demographic data and/or anonymized demographic trends are utilized to generate a current trend prediction for the user (e.g., the subject), in which the current trend prediction identifies expected pressures or when the user is expected to have an accident in the future. The data points established by the current trend prediction can be used to determine when to warn the user, caretakers of the user, or an autonomous system as to when the user is expected to have an accident.

After a warning is transmitted to the user, the caretakers of the user, and/or an autonomous system, may provide user feedback. In some embodiments of the present invention, the user feedback is obtained from the user and/or a caretaker of the user interacting with a user interface of a user device (e.g., user device 402). For example, in some embodiments of the present invention, the user feedback may indicate that the user or caretaker indicated whether an accident had occurred such as by clicking a button that says "good" to indicate no accident or clicking a button that says "incident" to indicate that an accident has occurred. In some embodiments of the present invention, the user feedback may indicate that the user or caretaker believes the warning was issued too soon such as by clicking a button that says "snooze."

The obtained feedback is mapped to the current trend prediction of the user to generate a real data trend that is predicted based on the obtained feedback. Pressure readings are obtained at a second time period subsequent to the first time period. For ease of explanation, the pressure readings obtained at the second time period are referenced herein as being "real-time" pressure readings as they are obtained subsequent to the readings obtained at the first time period. The demographic data and/or real data trend line are obtained and a predicted real data trend line is generated Similar to the above, the real-time pressure readings are utilized to compare the real-time pressure readings to the real data trend line. One or more of the established thresholds are adjusted based on the mapped user feedback.

Referring back to FIG. 4, in some embodiments of the present invention, assistance system 404 executes the machine learning algorithm by processing a machine learning model that is based on features that are extracted from pressure readings of pressure sensors 408 and/or feedback obtained from the subject and/or caretaker. In some embodiments of the present invention, assistance system 404 employs parallel computing to process portions of the pressure readings and/or feedback to search database 414 to identify relevant demographic data. For instance, in some embodiments of the invention, assistance system 404 performs parallel computing associated with two or more processors that process one or more portions of pressure readings and/or feedback in parallel. In one example, assistance system 404 executes a classification machine learning model using the features extracted from the pressure readings and/or feedback to generate trend lines, identifying when an accident is expected to occur, which caretaker to contact, and/or in which order to contact the caretakers. In some embodiments of the present invention, the pressure readings and feedback data is input from database 414, pressure sensors 408, and/or from user device 402. In some embodiments of the present invention, the classification machine learning model maps extracted features to one or more categories. In another example, assistance system 404 executes a regression machine learning model using extracted features. In some embodiments of the present invention, a regression machine learning model is used to determine relationships among pressure readings and/or feedback that indicate correlation between pressure readings and undeterred incidents. In yet another example, assistance system 404 executes a clustering machine learning model using a feature matrix that is populated based, at least in part, on the features that are extracted from the pressure readings data and/or feedback.

Figure 6:
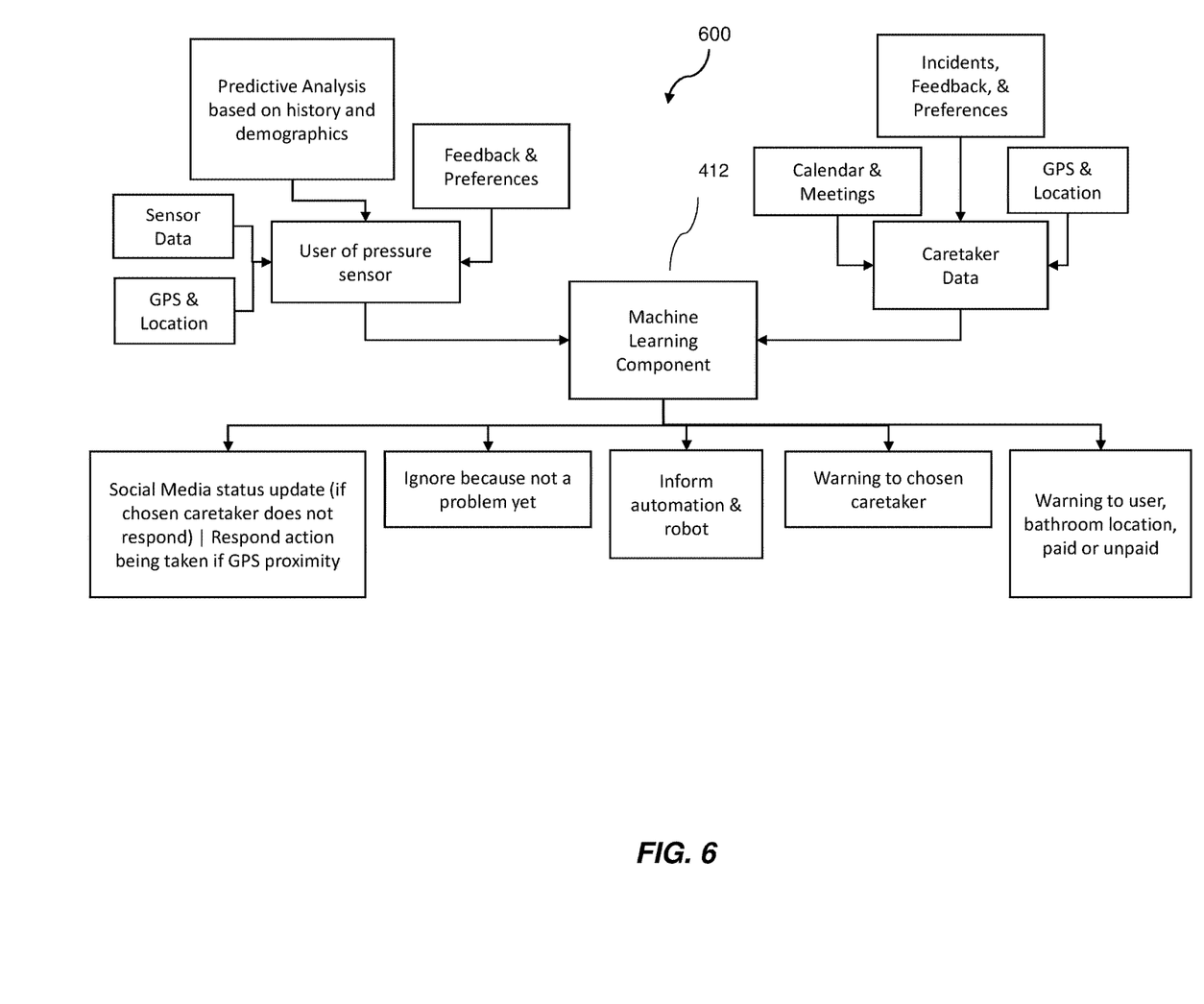
FIG. 6 depicts a block diagram illustrating example inputs and outputs of communication and warning component in accordance with one or more embodiments of the present invention.

FIG. 6 depicts a block diagram 600 illustrating example inputs and outputs of communication and warning component that are provided to machine learning component 412 in accordance with one or more embodiments of the present invention. In some embodiments of the present invention, machine learning component 412 provides user data (e.g., data of the subject) and caretaker data (e.g., caretaker of the subject). In some embodiments of the present invention, the user data includes sensor data, GPS & location data, predicating analysis data, feedback data, and/or preferences data of the user (e.g., the subject). In some embodiments of the present invention, the predictive analysis data is based on demographic data of a plurality of users and historical data of the user (e.g. prior pressure readings of the subject correlated with undeterred accidents). In some embodiments of the present invention, the caretaker data includes calendar and meeting data that is obtained from an application executed on a user device of the caretaker. In some embodiments of the present invention, the caretaker data further or alternatively includes GPS & location data, incident data, feedback data, and/or preferences data of the caretaker.

After having processed the input data by machine learning component 412, an electronic warning may be transmitted. In some embodiments of the present invention, the transmission of the electronic warning includes posting a social media status. For example, in some embodiments of the present invention, if a selected caretaker does not respond within a predetermined amount of time, a social media status may be updated to indicate that the user (e.g., the subject) is need of assistance. In some embodiments of the present invention, the transmission of the electronic warning includes transmitting a command to an automatic system such as a robot to perform a particular action such as to move a robotic arm, walk the subject to the restroom, contract or retract the bladder or bowels of the subject, etc. In some embodiments of the present invention, the transmission of the electronic warning includes transmitting a warning to a selected caretaker, in which the caretaker is selected based on availability and/or proximity of the caretaker to the user (e.g., which of a plurality of caretakers is presently located nearest to the subject). In some embodiments of the present invention, the transmission of the electronic warning includes transmitting a warning to the user recommending bathroom locations that are within a predetermined distance from the user. In some embodiments of the present invention, the electronic warning includes information regarding whether the recommended bathroom locations require payment to enter. In some embodiments of the present invention, a transmission of an electronic warning is not performed as the threshold has not yet been met (e.g., ignore when a problem has not yet been detected). In some embodiments of the present invention, the electronic warning message is transmitted according to a level of responsiveness of a caretaker, distance from the subject, and/or availability of access to a nearby place of relief (e.g., restroom). For example, in some embodiments of the present invention, if according to a generated tread line it is determined the subject is expected to need to relieve themselves within a first expected time (e.g., 20 minutes) and if the closest restroom to the subject takes a second amount of time to reach (e.g., restroom 15 minutes away), an electronic warning may be transmitted to the subject, the caretaker, or an autonomous system indicating that include the subject needs to use the bathroom within the first expected time and that the nearest restroom will take the second amount of time to reach.

Referring back to FIG. 4, as noted above, assistance system 404 is configured to assist incontinent subjects such as children, adults, and/or animals. The following is a non-limiting use case scenario illustrates an example implementation where the subject is an animal. Three roommates (Roommate 1, Roommate 2, and Roommate 3) have a dog that needs to be let out at irregular intervals perhaps due to a disease or inconsistent digestion. All the roommates are out when assistance system 404 receives a signal from pressure sensor 408 indicating that the bladder or bowels of the dog has exceeded a threshold. This threshold is established by machine learning component 412 of assistance system 404. Machine learning component 412 has learned through user feedback that incontinence will occur if the roommates are not notified at this threshold. Assistance system 404 is granted access to the roommates' phone applications and/or online accounts based on the preferences set by each roommate. Assistance system 404 then decides which roommate to warn by checking their calendar information, extracted from the phone of each of the roommates to determine whether any of the roommates are presently at a priority meeting, and then calculating the distance between each roommate and the location of the home. Assistance system 404 determines that Roommate 2 is closest and has no meetings scheduled. Roommate 2 is transmitted a warning message. However, Roommate 2 does not appear to be responding and GPS information shows he is no closer to the dog's location. Assistance system 404 then sends out a tweet to an account that was created for the dog. Roommate 1 then responds upon viewing the tweet as Roommate 2 was not responding.

The following is a non-limiting use case scenario that illustrates an example implementation where the subject is a user (e.g. human) and has a caretaker assisting him/her. The caretaker has granted assistance system 404 access to the caretaker's GPS and phone preferences data. Assistance system 404 then receives a signal from pressure sensor 408 indicating that the bladder or bowels of the user has exceeded a threshold for when to communicate that the user needs to use the bathroom when the caretakers are out of the house. Assistance system 404 detects through the GPS information of both the caretaker and the user, that the caretaker and the user are near each other and that they are both located outside of the house. Information about possible bathroom locations (paid or unpaid, depending on country) are sent to the caretaker via a preferred communication method as set by the phone settings of the caretaker (e.g., SMS message, email, etc.).

Figure 7:
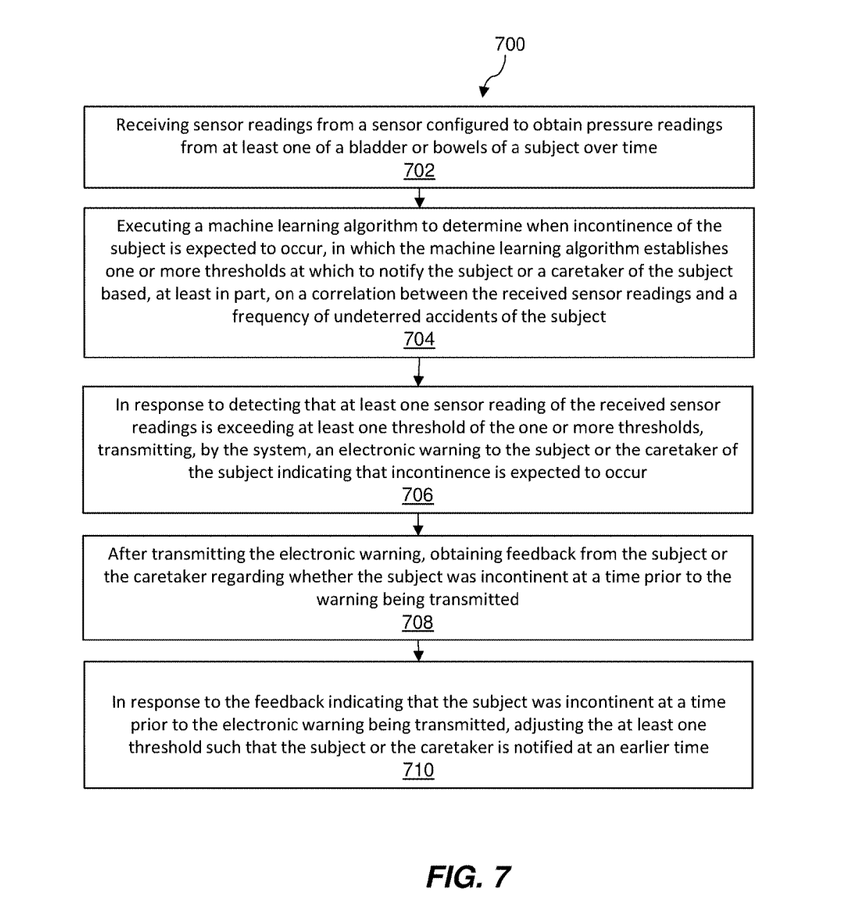
FIG. 7 depicts a flow diagram illustrating a methodology in accordance with one or more embodiments of the present invention.

Additional details of the operation of assistance system 404 will now be described with reference to FIG. 7, wherein FIG. 7 depicts a flow diagram illustrating a methodology 700 according to one or more embodiments of the present invention. At 702, sensor readings are received from a sensor that is configured to obtain pressure readings from at least one of a bladder or bowels of a subject over time. At 704, a machine learning algorithm is executed to determine when incontinence of the subject is expected to occur. The machine learning algorithm establishes one or more thresholds at which to notify an autonomous system, the subject and/or a caretaker of the subject, in which the one or more thresholds are established based, at least in part, on a correlation between the received sensor readings and a frequency of undeterred accidents of the subject. At 706, in response to having detected that at least one sensor reading of the received sensor readings is exceeding at least one threshold of the one or more thresholds, an electronic warning is transmitted to the autonomous system, the subject and/or the caretaker of the subject, indicating that incontinence is expected to occur. At 708, after having transmitted the electronic warning, feedback is obtained from the autonomous system, the subject, and/or the caretaker regarding whether the subject was incontinent at a time prior to the warning being transmitted. At 710, in response to the obtained feedback indicating that the subject was incontinent at a time prior to the electronic warning being transmitted, the at least one threshold is adjusted such that the subject or the caretaker is notified at an earlier time.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for assisting incontinent subjects comprising:
   receiving, by a system comprising one or more processors, sensor readings from a sensor configured to obtain pressure readings from at least one of a bladder or bowels of a subject over time;
   executing, by the system, a machine learning algorithm to determine when incontinence of the subject is expected to occur, wherein the machine learning algorithm establishes one or more thresholds at which to notify an autonomous system, the subject, or a caretaker of the subject, wherein the one or more thresholds are established based, at least in part, on a correlation between the received sensor readings and a frequency of undeterred accidents of the subject; and
   in response to detecting that at least one sensor reading of the received sensor readings is exceeding at least one threshold of the one or more thresholds, transmitting, by the system, an electronic warning to the autonomous system, the subject, or the caretaker of the subject indicating that incontinence is expected to occur.

2. The computer-implemented method of claim 1 further comprising:
   after transmitting the electronic warning, obtaining feedback from the autonomous system, the subject, or the caretaker regarding whether the subject was incontinent at a time prior to when the electronic warning was transmitted; and
   in response to the feedback indicating that the subject was incontinent at a time prior to when the electronic warning was transmitted, adjusting the at least one threshold such that the autonomous system, the subject, or the caretaker is notified at an earlier time.

3. The computer-implemented method of claim 1, wherein the establishing of the one or more thresholds includes generating a trend line of the received sensor readings and comparing the received sensor readings to anonymized demographic data of other subjects.

4. The computer-implemented method of claim 1, wherein transmitting the electronic warning to the autonomous system, the subject, or the caretaker of the subject includes:
   obtaining location information regarding a location of the subject and locations of a plurality of caretakers of the subject;
   identifying which of the plurality of caretakers is presently located nearest to the subject, wherein the identifying is based on the locations of the plurality of caretakers and the location of the subject; and
   transmitting the electronic warning to the identified caretaker.

5. The computer-implemented method of claim 4, wherein the electronic warning further includes an indication of the location of the subject.

6. The computer-implemented method of claim 1, wherein transmitting the electronic warning to the autonomous system, the subject, or the caretaker of the subject includes:
   obtaining location information regarding a location of the subject and locations of a plurality of caretakers of the subject;
   obtaining calendar information for each of the plurality of caretakers, wherein the calendar information includes a location of an event;
   identifying a subset of the plurality of caretakers that are not presently located at the event, wherein the identifying of the subset of caretakers is based on matching the locations of the plurality of caretakers to the location of the event;
   identifying, based on the locations of the plurality of caretakers and the location of the subject, which caretaker of the subset of caretakers is presently located nearest to the subject; and
   transmitting the electronic warning to the identified caretaker.

7. The computer-implemented method of claim 1, wherein transmitting the electronic warning to the autonomous system, the subject, or the caretaker of the subject includes transmitting at least one of a social media post, social media message, text message, phone alert, or email.

8. A computer program product for assisting incontinent subjects, the computer program product comprising a non-transitory computer readable storage medium having program instructions embodied therewith, the program instructions executable by a system comprising one or more processors to cause the system to perform a method, the method comprising:
   receiving, by the system, sensor readings from a sensor configured to obtain pressure readings from at least one of a bladder or bowels of a subject over time;
   executing, by the system, a machine learning algorithm to determine when incontinence of the subject is expected to occur, wherein the machine learning algorithm establishes one or more thresholds at which to notify an autonomous system, the subject, or a caretaker of the subject, wherein the one or more thresholds are established based, at least in part, on a correlation between the received sensor readings and a frequency of undeterred accidents of the subject; and
   in response to detecting that at least one sensor reading of the received sensor readings is exceeding at least one threshold of the one or more thresholds, transmitting, by the system, an electronic warning to the autonomous system, the subject, or the caretaker of the subject indicating that incontinence is expected to occur.

9. The computer program product comprising the non-transitory computer readable storage medium of claim 8, wherein the method further includes:
   after transmitting the electronic warning, obtaining feedback from the autonomous system, the subject, or the caretaker regarding whether the subject was incontinent at a time prior to when the electronic warning was transmitted; and
   in response to the feedback indicating that the subject was incontinent at a time prior to when the electronic warning was transmitted, adjusting the at least one threshold such that the autonomous system, the subject, or the caretaker is notified at an earlier time.

10. The computer program product comprising the non-transitory computer readable storage medium of claim 8, wherein the establishing of the one or more thresholds includes generating a trend line of the received sensor readings and comparing the received sensor readings to anonymized demographic data of other subjects.

11. The computer program product comprising the non-transitory computer readable storage medium of claim 8, wherein transmitting the electronic warning to the autonomous system, the subject, or the caretaker of the subject includes:
   obtaining location information regarding a location of the subject and locations of a plurality of caretakers of the subject;
   identifying which of the plurality of caretakers is presently located nearest to the subject, wherein the identifying is based on the locations of the plurality of caretakers and the location of the subject; and
   transmitting the electronic warning to the identified caretaker.

12. The computer program product comprising the non-transitory computer readable storage medium of claim 11, wherein the electronic warning further includes an indication of the location of the subject.

13. The computer program product comprising the non-transitory computer readable storage medium of claim 8, wherein transmitting the electronic warning to the autonomous system, the subject, or the caretaker of the subject includes:
   obtaining location information regarding a location of the subject and locations of a plurality of caretakers of the subject;
   obtaining calendar information for each of the plurality of caretakers, wherein the calendar information includes a location of an event;
   identifying a subset of the plurality of caretakers that are not presently located at the event, wherein the identifying of the subset of caretakers is based on matching the locations of the plurality of caretakers to the location of the event;
   identifying, based on the locations of the plurality of caretakers and the location of the subject, which caretaker of the subset of caretakers is presently located nearest to the subject; and
   transmitting the electronic warning to the identified caretaker.

14. The computer program product comprising the non-transitory computer readable storage medium of claim 8, wherein transmitting the electronic warning to the autonomous system, the subject, or the caretaker of the subject includes transmitting at least one of a social media post, social media message, text message, phone alert, or email.

15. A system for assisting incontinent subjects, the system comprising one or more processors configured to perform a method, the method comprising:
   receiving, by the system, sensor readings from a sensor configured to obtain pressure readings from at least one of a bladder or bowels of a subject over time;
   executing, by the system, a machine learning algorithm to determine when incontinence of the subject is expected to occur, wherein the machine learning algorithm establishes one or more thresholds at which to notify an autonomous system, the subject, or a caretaker of the subject, wherein the one or more thresholds are established based, at least in part, on a correlation between the received sensor readings and a frequency of undeterred accidents of the subject; and
   in response to detecting that at least one sensor reading of the received sensor readings is exceeding at least one threshold of the one or more thresholds, transmitting, by the system, an electronic warning to the autonomous system, the subject, or the caretaker of the subject indicating that incontinence is expected to occur.

16. The system of claim 15, wherein the method further includes:
   after transmitting the electronic warning, obtaining feedback from the subject or the caretaker regarding whether the subject was incontinent at a time prior when the electronic warning was transmitted; and
   in response to the feedback indicating that the subject was incontinent at a time prior to the electronic warning being transmitted, adjusting the at least one threshold such that the autonomous system, the subject, or the caretaker is notified at an earlier time.

17. The system of claim 15, wherein the establishing of the one or more thresholds includes generating a trend line of the received sensor readings and comparing the received sensor readings to anonymized demographic data of other subjects.

18. The system of claim 15, wherein transmitting the electronic warning to the autonomous system, the subject, or the caretaker of the subject includes:
   obtaining location information regarding a location of the subject and locations of a plurality of caretakers of the subject;
   identifying which of the plurality of caretakers is presently located nearest to the subject, wherein the identifying is based on the locations of the plurality of caretakers and the location of the subject; and
   transmitting the electronic warning to the identified caretaker.

19. The system of claim 15, wherein transmitting the electronic warning to the autonomous system, the subject, or the caretaker of the subject includes:
   obtaining location information regarding a location of the subject and locations of a plurality of caretakers of the subject;
   obtaining calendar information for each of the plurality of caretakers, wherein the calendar information includes a location of an event;
   identifying a subset of the plurality of caretakers that are not presently located at the event, wherein the identifying of the subset of caretakers is based on matching the locations of the plurality of caretakers to the location of the event;
   identifying, based on the locations of the plurality of caretakers and the location of the subject, which caretaker of the subset of caretakers is presently located nearest to the subject; and
   transmitting the electronic warning to the identified caretaker.

20. The system of claim 15, wherein transmitting the electronic warning to the autonomous system, the subject, or the caretaker of the subject includes transmitting at least one of a social media post, social media message, text message, phone alert, or email.

* * * * *